United States Patent
Van Laar et al.

(10) Patent No.: US 7,468,461 B2
(45) Date of Patent: Dec. 23, 2008

(54) METHOD FOR THE PRODUCTION OF AMINES

(75) Inventors: Frederik Van Laar, Limburgerhof (DE); Ekkehard Schwab, Neustadt (DE); Steffen Oehlenschlaeger, Ludwigshafen (DE); Hartwig Voss, Frankenthal (DE); Wolfgang Mackenroth, Bad Duerkheim (DE); Konrad Morgenschweis, Dresden (DE); Ulrich Penzel, Tettau (DE); Bernd Weidner, Wormlage (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/057,617

(22) Filed: Mar. 28, 2008

(65) Prior Publication Data

US 2008/0177111 A1    Jul. 24, 2008

Related U.S. Application Data

(62) Division of application No. 10/575,924, filed as application No. PCT/EP2004/011642 on Oct. 15, 2004.

(30) Foreign Application Priority Data

Oct. 17, 2003   (DE)   ................. 103 49 095

(51) Int. Cl.
*C07C 209/00*   (2006.01)
*B01J 23/89*    (2006.01)

(52) U.S. Cl. ....................... 564/423; 502/185
(58) Field of Classification Search ................. 564/423; 502/185

See application file for complete search history.

(56) References Cited

U.S. PATENT DOCUMENTS

| | | | |
|---|---|---|---|
| 3,127,356 A | 3/1964 | Hamilton et al. | |
| 3,637,820 A * | 1/1972 | Dodman et al. | 562/68 |
| 4,185,036 A | 1/1980 | Cossaboon | |
| 4,237,070 A * | 12/1980 | Patterson et al. | 564/423 |
| 4,256,671 A * | 3/1981 | Hildreth et al. | 564/422 |
| 5,214,212 A | 5/1993 | Whitman | |
| 5,728,880 A * | 3/1998 | Beckhaus et al. | 564/305 |
| 5,759,944 A | 6/1998 | Buchanan et al. | |
| 5,973,206 A * | 10/1999 | Laitinen | 564/423 |
| 6,242,649 B1 * | 6/2001 | Beckhaus et al. | 564/422 |
| 6,818,720 B2 * | 11/2004 | Krauter et al. | 502/257 |
| 6,965,053 B2 * | 11/2005 | Forlin et al. | 564/423 |

FOREIGN PATENT DOCUMENTS

| | | |
|---|---|---|
| DE | 39 28 329 | 2/1991 |
| DE | 196 36 214 | 1/1998 |
| DE | 199 11 865 | 9/2000 |
| EP | 0 124 010 | 11/1984 |
| EP | 0458006 A1 * | 11/1991 |
| EP | 0 595 124 | 5/1994 |
| EP | 0 768 917 | 4/1997 |
| WO | 03/039743 | 5/2003 |

OTHER PUBLICATIONS

Matsumura, Yasuyuki et al., "Synergetic effect of nickel and platinum supported on silica in catalytic methanol decomposition", Chemical Communications, pp. 657-658, 1997.
Renouprez, A. J. et al., "Catalytic Activity of Alumina Supported Platinum-Nickel Alloys", Studies in Surface Science and Catalysis 7A, pp. 173-185, 1981.

* cited by examiner

*Primary Examiner*—Porfirio Nazario Gonzalez
(74) *Attorney, Agent, or Firm*—Oblon, Spivak, McClelland, Maier & Neustadt, P.C.

(57) ABSTRACT

The present invention provides a process for hydrogenating aromatic nitro compounds to the corresponding amines in the presence of hydrogenation catalysts, which comprises using hydrogenation catalysts in which nickel and platinum are present on a support in the form of an alloy having an atomic ratio of nickel to platinum in the alloy of between 30:70 and 70:30.

14 Claims, No Drawings

METHOD FOR THE PRODUCTION OF AMINES

This application is a Divisional of U.S. application Ser. No. 10/575,924, filed Apr. 14, 2006, now pending; which is a which is a 371 of PCT/EP04/11642, filed Oct. 15, 2004.

The invention relates to a process for preparing amines by catalytically hydrogenating the corresponding nitro compounds, and also novel catalysts for carrying out this process.

The preparation of amines, in particular of aromatic mono-, di- and/or polyamines, by catalytically hydrogenating the corresponding mono-, di- and/or polynitro compounds has been known for some time and is described many times in the literature. An aromatic amine which is frequently used in industry is tolylenediamine (TDA) which may be further processed to tolylene diisocyanate and is prepared by hydrogenating dinitrotoluene (DNT). A problem in the hydrogenation of DNT is the increased formation of by-products; in addition to low boilers, usually deaminated and ring-hydrogenated products, high molecular weight or tarlike products frequently occur and not only reduce the yield of the process but may also lead to premature deactivation of the catalyst.

Useful hydrogenation catalysts, as described, for example, in EP-A-0 124 010, are frequently metals of transition group VIII of the Periodic Table, in particular Raney iron, Raney cobalt and Raney nickel.

Frequently, catalysts are also used for the hydrogenation of nitroaromatics and comprise noble metals, in particular palladium, or else platinum. Also known in this context are catalysts which comprise platinum and nickel.

For instance, U.S. Pat. No. 3,127,356 describes a process for preparing hydrogenation catalysts for the hydrogenation of DNT to TDA. The catalysts comprise a support, an oleophilic hydrocarbon component, for example carbon black, to which the metals are applied. In this case, the nickel is present in the catalyst as the oxide or hydroxide.

U.S. Pat. No. 5,214,212 describes a process for ring-hydrogenating aromatic amines. The catalyst used is a noble metal catalyst which may additionally be doped with further metals, including nickel. The noble metal used may be platinum in a mixture with other noble metals. The noble metals are present in the catalyst as metals and the doped metals in the form of salts.

DE 39 28 329 describes a process for preparing chlorine-substituted aromatic amines from the corresponding nitro compounds. The catalyst used in this process consists of activated carbon as a support, to which platinum and a further metal, in particular nickel, are applied.

EP 595 124 describes a process for preparing chlorine-substituted aromatic amines from the corresponding nitro compounds. The catalyst used comprises platinum and nickel on activated carbon. In this process, platinum is initially applied to the activated carbon and reduced and then nickel is applied to the support in the form of a salt. The nickel is present in this catalyst as the hydroxide.

EP 768 917 describes a catalyst for preparing carboxylic acid salts. This consists of an anchor metal, for example platinum, some of which is embedded in an alkali-resistant support, and at least some of which has been coated by electroless deposition with a catalytically active non-noble metal, for example nickel. In this catalyst, the two metals are present on the support as separate phases.

U.S. Pat. No. 4,185,036 describes a process for hydrogenating mixtures of nitroaromatics. The catalysts used comprise platinum and if appropriate a further metal, for example nickel, on activated carbon. The further metal is present in the form of the oxide or hydroxide on the support.

DE 199 11 865 and DE 196 36 214 describe processes for hydrogenating dinitrotoluene. The catalysts used comprise iridium and also at least one doping element, for example nickel or platinum.

WO 03/39743 describes a process for preparing TDA using a hydrogenation catalyst consisting of platinum, a further noble metal and a non-noble metal.

It is an ever-present object when hydrogenating DNT to TDA to further increase the yield and in particular to improve the selectivity of the process, in order thus to suppress the side reactions which lead to the formation of high molecular weight by-products or to the formation of low boilers. In addition, the catalyst should be stable even at relatively high reaction temperatures and not permit any deterioration in the selectivity of the process.

It is an object of the present invention to provide catalysts for the hydrogenation of aromatic nitro compounds to the corresponding amines, in particular of DNT to TDA, which lead to a higher yield and selectivity of the process and do not permit any deterioration in the process control even at relatively high reaction temperatures.

We have found that this object is achieved by the use of hydrogenation catalysts in which platinum and nickel are present in the form of an alloy on a support.

The present invention thus provides a process for hydrogenating aromatic nitro compounds to the corresponding amines, in particular tolylenediamine by catalytically hydrogenating dinitrotoluene, in the presence of hydrogenation catalysts, which comprises using hydrogenation catalysts in which nickel and platinum are present on a support in the form of an alloy having an atomic ratio of nickel to platinum in the alloy of between 30:70 and 70:30.

Alloys of platinum and nickel having other atomic ratios can in principle also be used for the process according to the invention, but lead, especially when carrying out the hydrogenation at relatively high temperatures, to low yields of TDA.

The atomic ratio of nickel to platinum is in particular between 45:55 and 55:45. The atomic ratio was determined by means of EDXS (energy dispersive X-ray spectroscopy).

The catalyst usually comprises finely crystalline metal particles of the Pt—Ni alloy which are of from approx. 1 to 15 nm in size and are distributed on the carbon particles. In places, Ni—Pt particle agglomerates or aggregates which are from 1 to 2 mm in size may occur on the support, but also individual pure Ni or Pt particles. The electron diffraction lines of the metal particles are between those of Pt and Ni, which provides additional confirmation of alloy formation. The metal particles are usually polycrystalline, and may be characterized with a high-resolution TEM (FEG-TEM: Field Emission Gun-Transmission Electron Microscopy).

The support used for the catalysts may be the customary and known materials for this purpose. Preference is given to using activated carbon, carbon black, graphite or metal oxides, preferably hydrothermally stable metal oxides, for example $ZrO_2$, $TiO_2$. In the case of graphite, particular preference is given to HSAG (high surface area graphite) having a surface area of from 50 to 300 $m^2/g$. Particular preference is given to the physically or chemically activated carbons or carbon blacks, such as acetylene black.

The catalyst used in accordance with the invention is preferably used in an amount of from 0.01 to 10% by weight, preferably from 0.1 to 5% by weight, more preferably from 0.2 to 2% by weight, based on the reaction mixture.

The catalyst is usually introduced into the reactor in the reduced and passivated state. The reduced and passivated state of the catalyst means that the catalyst has been activated after the preparation, but, for safety reasons, the active centers have been passivated, for example by passing over oxygen or carbon dioxide. Alternatively, the catalyst may be conditioned and stabilized under an inert atmosphere or in a nonflammable solvent, for example in water, TDA/water or higher alcohols such as butanol or ethylene glycol.

The process according to the invention may be carried out continuously or batchwise using customary reactors with customary process parameters such as pressure and temperature.

Preference is given to carrying out the hydrogenation according to the invention at pressures in the range from 5 to 100 bar, more preferably from 10 to 40 bar, in particular from 20 to 25 bar.

Preference is given to carrying out the hydrogenation according to the invention at a temperature in the range from 80 to 250° C., more preferably in the range from 100 to 220° C. and in particular in the range from 160 to 200° C.

Usually, the hydrogenation is carried out in the form of a continuous suspension hydrogenation in customary and suitable reactors. Useful reactors are, for example, stirred tanks or loop reactors, for example jet-loop reactors, loop Venturi reactors, or loop reactors having internal flow circulation, as described in WO 00/35852. To remove the catalysts from the discharged reaction mixture, for example, crossflow filters may be used. Such a process is described, for example, in WO 03/66571.

The hydrogenation gases used may be any desired gases which comprise free hydrogen and no harmful amounts of catalyst poisons, for example carbon monoxide. For example, reformer offgases may be used. Also possible are mixtures of hydrogen with nitrogen and/or carbon dioxide, as described, for example, in DE 10105277. However, preference is given to using pure hydrogen as the hydrogenating gas.

The amines formed in the hydrogenation are removed continuously or batchwise from the hydrogenation procedure and subjected to a workup, for example a distillative aftertreatment.

Preference is given in the process according to the invention to using aromatic nitro compounds having one or more nitro groups and from 6 to 18 carbon atoms, for example nitrobenzenes, e.g. o-, m-, p-nitrobenzene, 1,3-dinitrobenzene, nitrotoluenes, e.g. 2,4-, 2,6-dinitrotoluene, 2,4,6-trinitrotoluene, nitroxylenes, e.g. 1,2-dimethyl-3-, 1,2-dimethyl-4-, 1,4-dimethyl-2-, 1,3-dimethyl-2-, 2,4-dimethyl-1- and 1,3-dimethyl-5-nitrobenzene, nitronaphthalenes, e.g. 1-, 2-nitronaphthalene, 1,5- and 1,8-dinitronaphthalene, chloronitrobenzenes, e.g. 2-chloro-1,3-, 1-chloro-2,4-dinitrobenzene, o-, m-, p-chloronitrobenzene, 1,2-dichloro-4-, 1,4-dichloro-2-, 2,4-dichloro-1- and 1,2-dichloro-3-nitrobenzene, chloronitrotoluenes, e.g. 4-chloro-2-, 4-chloro-3-, 2-chloro-4- and 2-chloro-6-nitrotoluene, nitroanilines, e.g. o-, m-, p-nitroaniline; nitroalcohols, e.g. tris(hydroxymethyl)nitromethane, 2-nitro-2-methyl-, 2-nitro-2-ethyl-1,3-propanediol, 2-nitro-1-butanol and 2-nitro-2-methyl-1-propanol, and also any mixtures of two or more of the nitro compounds mentioned.

Preference is given to using the process according to the invention to hydrogenate aromatic nitro compounds, preferably mononitrobenzene, methylnitrobenzene or methylnitrotoluene, and in particular 2,4-dinitrotoluene or its technical mixtures with 2,6-dinitrotoluene, and these mixtures preferably have up to 35 percent by weight, based on the total mixture, of 2,6-dinitrotoluene with fractions of from 1 to 5% of vicinal DNT and from 0.5 to 1.5% of 2,5- and 3,5-dinitrotoluene, to the corresponding amines.

In the process according to the invention, the aromatic nitro compound may be used in pure form, as a mixture with the corresponding di- and/or polyamine, as a mixture with the corresponding di- and/or polyamine and water, as a mixture with the corresponding di- and/or polyamine, water and an alcoholic solvent or as a mixture with the corresponding di- and/or polyamine, water, an alcoholic solvent and a catalyst-reactivating additive, and mixtures of two or more of the abovementioned nitro compounds, the corresponding amine compounds, the alcoholic solvent and the catalyst-reactivating additive may also be used.

When a mixture as described above is used, the ratio of amine compound to water is preferably in the range from 10:1 to 1:10, more preferably in the range from 4:1 to 1:1, and the ratio of the amine/water mixture to at least one alcoholic solvent is preferably from 1000:1 to 1:1, more preferably from 50:1 to 5:1.

As is evident from the aforesaid, the hydrogenation in the process according to the invention may be carried out in the absence or in the presence of an alcoholic solvent and of a catalyst-reactivating additive.

Where an alcoholic solvent and a catalyst-reactivating additive are used, it will be appreciated that mixtures of two or more thereof may also be used.

Useful alcoholic solvents are lower aliphatic alcohols having from 1 to 6 carbon atoms, preferably methanol, ethanol or propanol individually, or a mixture of two or more thereof.

The catalyst-reactivating additives used are preferably aprotic solvents, in particular DMF, dioxane or THF, or a mixture of two or more thereof.

The amount of the alcoholic solvent and of the catalyst-reactivating additives used in the process according to the invention is not restricted in any particular manner and may be freely selected as required.

However, it is surprisingly also possible to carry out the hydrogenation of aromatic nitro compounds by the process according to the invention without the use of solvents. This procedure simplifies the workup of the reaction mixture after the hydrogenation; side reactions with the solvents are also fully suppressed.

In order to suppress side reactions, preference is given to conducting the process in such a way that the catalyst is used at its loading limit. This may be controlled, for example, by the amount of the nitro compound metered in, the amount of the catalyst in the reaction mixture, the temperature or the pressure.

The loading limit of the catalyst means the amount of hydrogenatable groups comprising nitrogen and oxygen atoms which may be hydrogenated by the catalyst under given pressure and temperature conditions. The groups comprising nitrogen and oxygen atoms may be not only nitro groups but also nitroso groups and hydroxylamine groups.

The catalysts according to the invention are prepared, for example, by initially charging the support and combining it with an aqueous solution of the platinum and nickel salts. The amount of the water used to dissolve the salts is such that a kneadable paste results. Preference is given to using the water in an amount of from 100 to 200% by weight of the support mass. Useful metal salts are in particular nitrates or chlorides, and preference is given to nitrates owing to their low corrosivity. The paste is mixed and then the water is evaporated under reduced pressure and temperatures in the range between 50 and 100° C., for example in a rotary evaporator or an oven. For safety reasons, the evaporation may be effected in a nitrogen stream. When chlorides are used as the metal salts, the metals can be fixed on the support by reducing with hydrogen. However, this may result in the occurrence of corrosion. Preference is therefore given to fixing the metals under alkaline conditions. This is effected in particular by adding an aqueous solution of alkali metal carbonates and subsequently washing the support to free it of anions. Alternatively, the metals may also be precipitated on the support from a supernatant solution under alkaline conditions, in particular at a pH in the range from 8 to 9. Afterwards, the support is dried, preferably as described above, and reduced with hydrogen. This may be effected, for example, in a rotary sphere furnace. Before the catalyst is conditioned, it is passivated, for example under an inert gas such as nitrogen which comprises traces of air, preferably not more than 10% by volume.

The use of the catalysts according to the invention makes it possible to carry out the hydrogenation of DNT to TDA even at temperatures in the range between 160 and 250° C., in particular from 160 to 200° C., at which the selectivity of the reaction deteriorates sharply when conventional catalysts are used. An increase in the reaction temperature is advantageous, since the solubilities of the individual components are higher, and the reaction rate also increases with temperature. The STY (space-time yield) can thus be increased, as long as the energy of reaction can be safely removed. An increase in the reaction temperature is advantageous, since the energy of reaction may be utilized at relatively high temperature, for example by steam generation. This is certainly economically viable for temperatures above 160° C. The amount of steam generated may then be used, for example, to activate cooling units, or in order to operate endothermic reactions.

The invention is illustrated by the examples which follow.

EXAMPLE 1

A Norit® SX+activated carbon support was initially charged in a dish and platinum(II) nitrate for 3% by weight of platinum, based on the weight of the catalyst, and nickel(II) nitrate hexahydrate for 1% by weight of nickel, based on the weight of the catalyst, were dissolved in water in an amount of 100% by weight of the amount of the support and added to the support in such a way as to give a kneadable paste. The paste was mixed thoroughly. The water solvent was evaporated in a rotary evaporator with gentle boiling at 60° C. and a pressure of from 0.2 to 0.4 bar. The metals were fixed under alkaline conditions on the support by adding a solution of sodium carbonate in an amount of 16% by weight of the amount of support in 100% by weight of the amount of support of water, and the sample was washed to free it of nitrate. The catalyst obtained in this way was dried at 80° C., before it was reduced in a rotary sphere oven under a hydrogen stream at 400° C. for 4 hours. Before the conditioning, the catalyst was passivated at room temperature in diluted air (5% by volume of air in nitrogen). The catalyst obtained in this way is referred to as catalyst A.

The catalyst obtained in this way had a content of 2.9% by weight of platinum and 0.97% by weight of nickel. This corresponded to an atomic ratio of 48:52.

EXAMPLE 2

Comparative

The procedure of Example 1 was repeated, except that only nickel salt for 0.25% by weight of nickel was used. The catalyst obtained in this way is referred to as catalyst B. The atomic ratio of platinum to nickel was 78:22.

EXAMPLE 3

Comparative

The support used in Example 1 was suspended in water to give a 10% suspension. To this end, the metal salts described in Example 1 were added in the ratio described in Example 1 and boiled to reflux with ammonium formate for 2 hours. The catalyst obtained in this way was washed to free it of nitrate. In this procedure, the platinum was reduced; the nickel was present on the support in the form of a hydroxide or oxide. The catalyst obtained in this way is referred to as catalyst C. In this catalyst, platinum and nickel were not present as an alloy, but rather in the form of discrete particles.

EXAMPLE 4

The procedure of Example 3 was repeated, except that no nickel salt was added. The catalyst obtained in this way is referred to as catalyst D.

Catalyst E (5% Pd/C)
Commercial, 5% by weight of activated carbon, Pd-comprising reference catalyst (50% water-moist).

Catalyst F
Commercial nickel catalyst on a $ZrO_2$ support.

EXAMPLE 5

Hydrogenation of DNT to TDA

The hydrogenation of DNT to TDA was carried out in a 300 ml continuous stirred tank; the catalyst was retained in the reactor mechanically.

The catalyst was suspended in water and introduced in the reactor (amount of catalyst from 1 to 2% by weight of the liquid volume of the reactor); DNT was continuously metered in as a melt, brought to temperature under an $H_2$ pressure of 22 bar, in such an amount that a space-time yield of 400 $kg_{TDA}/m^3$,h was attained. Samples were analyzed by means of gas chromatography: the TDA yield, formation of high boilers and low boilers was monitored. The space-time yield at low temperature (125° C.) was approx. 400 $kg_{TDA}/m^3$,h; at higher temperature, it was varied from 400 to 700 $kg_{TDA}/m^3$, h. At even higher space-time yields, the reaction temperature rose further, as a result of the limited cooling performance of the reactor.

The temperatures and the results can be taken from Table 1.

TABLE

| Example | Catalyst | Temperature | STY ($kg_{TDA}/m^3$, h) | TDA (%) |
|---|---|---|---|---|
| 1. Comparative | F | 125° C. | Approx. 400 | 98.9 |
|  | F | 180° C. | Catalyst is not stable | — |
| 2. Comparative | E | 140° C. | Approx. 400 | 98.0 |
|  | E | 180° C. | Approx. 400 | approx. 75 |
| 3. Comparative | D | 125° C. | Approx. 400 | 99.2 |
|  | D | 180° C. | Approx. 400 | 98.7 |
|  | D | 180° C. | Approx. 700 | 98.8 |
| 4. Comparative | C | 180° C. | Approx. 700 | 99.1 |
| 5. Comparative | B | 180° C. | Approx. 700 | 98.9 |
| Inventive | A | 180° C. | Approx. 700 | 99.3 |
|  | A | 140° C. | Approx. 400 | 99.5 |

The examples show that the commercial catalyst F results in very good yields at low temperature, and that the catalyst E is distinctly inferior to the catalyst F. Catalyst D results in very good yield at low temperature; it is low at higher temperature.

An increase in the catalyst loading, for example by increasing the space-time yield, may improve the TDA selectivity a little. Only with catalyst A can a high selectivity be achieved both at high and at low temperatures.

We claim:

1. A process comprising hydrogenating an aromatic nitro compound to the corresponding amine in the presence of a hydrogenation catalyst comprising nickel and platinum, wherein said nickel and platinum are present on a support in the form of an alloy having an atomic ratio of nickel to platinum in the alloy of 30:70 to 70:30.

2. The process according to claim 1, wherein the aromatic nitro compound is dinitrotoluene.

3. The process according to claim 1, wherein the atomic ratio of nickel to platinum in the alloy is 40:60 to 60:40.

4. The process according to claim 1, wherein the atomic ratio of nickel to platinum in the alloy is 45:55 to 55:45.

5. The process according to claim 1, wherein the catalyst is present in an amount of from 0.01 to 10% by weight, based on the total weight of the reaction mixture.

6. The process according to claim 1, wherein the catalyst is present in an amount of from 0.1 to 5% by weight, based on the total weight of the reaction mixture.

7. The process according to claim 1, wherein the catalyst is present in an amount of from 0.2 to 2% by weight, based on the total weight of the reaction mixture.

8. The process according to claim 1, wherein hydrogenation is carried out at a temperature of from 80 to 250° C.

9. The process according to claim 1, wherein the catalyst is present at its loading limit.

10. The process according to claim 1, wherein the support is selected from the group consisting of activated carbon, carbon black, graphite and metal oxide.

11. The process according to claim 1, wherein the catalyst is in the form of crystalline metal particles of Pt—Ni alloy which are of from 1 to 15 nm in size and are distributed on carbon particles.

12. The process according to claim 1, wherein aromatic nitro compound is dinitrotoluene, the corresponding amine is tolylenediamine, the hydrogenation is carried out at a pressure of 5 to 100 bar at a temperature of from 80 to 250° C.

13. The process according to claim 12, wherein the catalyst is in the form of crystalline metal particles of Pt—Ni alloy which are of from 1 to 15 nm in size and are distributed on carbon particles.

14. The process according to claim 13, wherein the atomic ratio of nickel to platinum in the alloy is 40:60 to 60:40 and the hydrogenation is carried out at a pressure of 20 to 25 bar.

* * * * *